United States Patent [19]

Ogata et al.

[11] Patent Number: 4,463,011
[45] Date of Patent: Jul. 31, 1984

[54] BIS-IMIDAZOLYL-BIS-PHENYLMETHANE DERIVATIVES AND THEIR USE AS FUNGICIDES

[75] Inventors: Masaru Ogata, Hyogo; Katsuya Tawara, Osaka; Yoshihachi Watanabe, Shiga; Hiroshi Matsumoto, Osaka; Toshio Takahashi, Hyogo, all of Japan

[73] Assignee: Shionogi & Co., Ltd., Osaka, Japan

[21] Appl. No.: 341,634

[22] Filed: Jan. 22, 1982

Related U.S. Application Data

[62] Division of Ser. No. 157,166, Jun. 6, 1980, Pat. No. 4,328,348.

[30] Foreign Application Priority Data

Jun. 7, 1979 [JP] Japan .................................. 54-71953
Sep. 7, 1979 [JP] Japan ................................ 54-115465

[51] Int. Cl.³ .................... A01N 43/50; C07D 403/02
[52] U.S. Cl. ................................. 424/273 R; 548/336
[58] Field of Search ..................... 548/336; 424/273 R

[56] References Cited

U.S. PATENT DOCUMENTS 3,985,766 10/1976 Regel et al. .................... 548/336

*Primary Examiner*—John M. Ford
*Assistant Examiner*—Kurt G. Briscoe
*Attorney, Agent, or Firm*—Birch, Stewart, Kolasch & Birch

[57] ABSTRACT

Benzylimidazole derivatives of the formula:

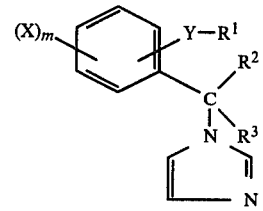

wherein
X is halogen, nitro, alkyl, alkoxy, or halobenzyloxy;
m is an integer of 0 to 3;
Y is oxa, thia or substituted- or unsubstituted-imino;
$R^1$ is alkyl, dialkylaminoaklyl, dibenzylaminoalkyl, 1-pyrrolidinyl, 2-imidazolin-2-yl, or a group of —(CH₂)n—Z—Q
(wherein n is an integer of 0 to 4; Z is oxa, thia, or a single bond; and Q is substituted- or unsubstituted-phenyl or thienyl)

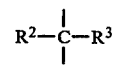

is methylene, 1-(1-imidazolyl)-1-methylmethylene, 1-(1-imidazolyl)-1-phenylmethylene, 1-phenylmethylene, or substituted or unsubstituted alkylidene;
the benzene ring of the above formula being optionally condensed with another benzene ring
with the proviso that when

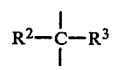

is methylene said benzene ring is condensed with another benzene ring, and acid addition salts thereof which are useful as an antimycotic drug or agricultural fungicide.

9 Claims, No Drawings

BIS-IMIDAZOLYL-BIS-PHENYLMETHANE DERIVATIVES AND THEIR USE AS FUNGICIDES

This application is a divisional of copending application Ser. No. 157,166, filed on June 6, 1980, now U.S. Pat. No. 4,328,348, which issued on May 4, 1982.

SUMMARY OF THE INVENTION

This invention relates to novel benzylimidazole derivatives useful as an antimycotic drug or agricultural fungicide. Such compounds are, for example, disclosed in Japanese Unexamined Patent Publication No. 50-148357 and the European Journal of Medicinal Chemistry 14, No. 3, pp 227~230, 231~237, 243~245 (1979). But the compounds of the following formula (I) are novel.

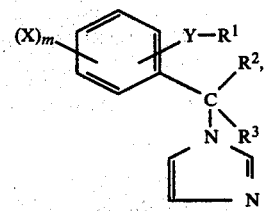

(I)

wherein
X is halogen, nitro, $C_1$ to $C_5$ alkyl, $C_1$ to $C_5$ alkoxy or halo-benzyloxy;
m is an integer of 0 to 3;
Y is oxa, thia or imino optionally substituted by $C_1$ to $C_5$ alkanoyl, $C_1$ to $C_5$ halo-alkanoyl or $C_1$ to $C_5$ alkyl;
$R^1$ is $C_1$ to $C_5$ alkyl, $C_3$ to $C_{10}$ dialkylaminoalkyl, $C_{15}$ to $C_{20}$ dibenzylaminoalkyl, 1-pyrrolidinyl, 2-imidazolin-2-yl, or a group of $—(CH_2)_n—Z—Q$ (wherein n is an integer of 0 to 4; Z is oxa, thia, or a single bond; Q is phenyl or thienyl optionally substituted by 1 to 3 members selected from halogen, nitro, $C_1$ to $C_5$ alkyl, and $C_1$ to $C_5$ alkoxy);

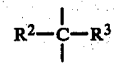

is methylene, 1-(1-imidazolyl)-1-methylmethylene, 1-(1-imidazolyl)-1-phenylmethylene, 1-phenylmethylene, or $C_1$ to $C_5$ alkylidene optionally substituted by phenyl;
the benzene ring of the above formula being optionally condensed with another benzene ring
with the proviso that when

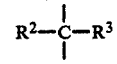

is methylene said benzene ring is condensed with another benzene ring, and pharmaceutically acceptable acid addition salts thereof.

DETAILED EXPLANATION

In the above general formula, halogen means chloro, bromo, fluoro and iodo, preferably chloro. $C_1$ to $C_5$ Alkyl means methyl, ethyl, propyl, isopropyl, butyl, sec-butyl, pentyl, isopentyl, and the like and $C_1$ to $C_5$ alkoxy means methoxy, ethoxy, propoxy, isopropoxy, butyloxy, sec-butyloxy, pentyloxy, isopentyloxy, and the like. $C_1$ to $C_5$ Alkanoyl means formyl, acetyl, propionyl, butyryl, and the like. $C_3$ to $C_{10}$ Dialkylaminoalkyl means dimethylaminoethyl, diethylaminoethyl, dipropylaminobutyl, methylethylaminoethyl, and the like. $C_1$ to $C_5$ Alkylidene means methylene, ethylidene, propylidene, isopropylidene, butylidene, pentylidene, and the like.

Compounds (I) can be easily converted to the corresponding pharmaceutically acceptable acid addition salts, which are included within the scope of this invention. Representative acids which can form the pharmaceutically acceptable salts are organic acids such as acetic acid, citric acid, tartaric acid, methanesulfonic acid, malic acid, succinic acid, oxalic acid, salicylic acid, or the like and inorganic acids such as hydrochloric acid, hydrobromic acid, sulfuric acid, nitric acid, phosphoric acid, or the like.

PREPARATION

Compounds (I) may be prepared according to the following scheme:

First Step

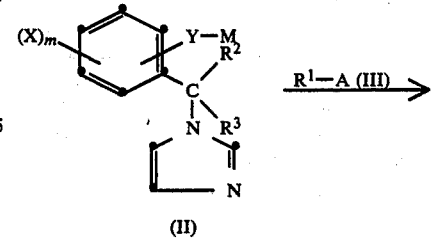

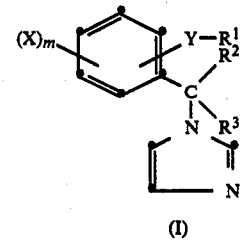

Second Step

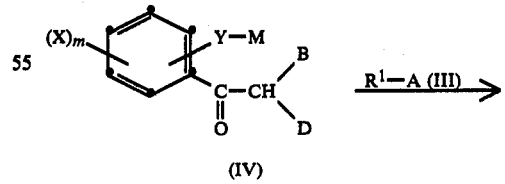

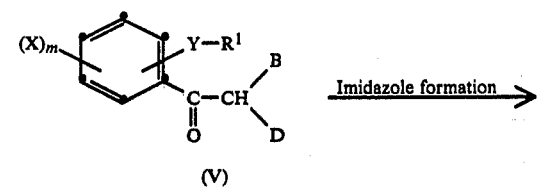

-continued

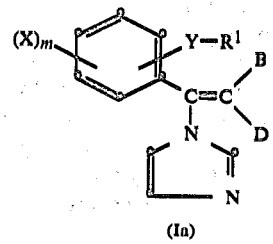

(wherein
M is hydrogen or alkali metal;
A is halogen or an ester residue;
B and D each is hydrogen or alkyl; and
X, m, Y, $R^1$, $R^2$ and $R^3$ each has the same significance as given earlier)

(First Step)

This process may be carried out by reacting Compound (II) with Compound (III) in the presence of a base in an inert solvent at room temperature or under heating. Representative bases are sodium hydroxide, potassium hydroxide, sodium hydride, sodium amide, potassium amide, sodium ethoxide, potassium carbonate, and the like. Representative inert solvents are dimethylformamide, benzene, methanol, chloroform, dioxane, tetrahydrofuran, acetone, and the like.

The starting compound (II) is available, for example, by treating the ketone (IV) with N,N'-thionyldiimidazole or N,N'-carbonyldiimidazole for imidazole formation. The reaction is carried out in an inert solvent such as methylene chloride, chloroform, tetrahydrofuran, dioxane, benzene, acetonitrile, or 1,2-dichloroethane at room temperature or under cooling.

(Second Step)

The reaction of the starting compound (IV) with the compound (III) may be carried out in the same manner as in the First Step. Then the intermediate (V) is subjected to the imidazole formation in the same manner as in the above preparation of the starting compound (II).

EFFECT

Compounds (I) and the pharmaceutically acceptable salts thereof prepared in this invention exhibit excellent antimycotic activities and are useful as an antimycotic drug for humans and animals.

Minimum Inhibitory Concentration (MIC, μ/ml) in vitro of some typical Compounds (I) are indicated in the following Table 1. The compound numbers correspond to the structure of the products prepared in the respective numbered Examples.

TABLE 1

| Fungi Compound No. | MIC Values (γ/ml) | | |
|---|---|---|---|
| | Aspergillus fumigates | Candida albicans M-9 | Trichophyton asteroides |
| 1 | 3.1 | 6.2 | ≤0.1 |
| 7 | 1.6 | 100.0 | ≤0.1 |
| 8 | 1.6 | 25.0 | 50.0 |
| 13 | 1.6 | 6.2 | ≤0.1 |
| 17 | 3.1 | 3.1 | ≤0.1 |
| 22 | 1.6 | 6.2 | ≤0.1 |
| 28 | 6.2 | 12.5 | ≤0.1 |
| 34 | 6.2 | 50.0 | 1.6 |
| 39 | 0.4 | 6.2 | ≤0.1 |
| 40 | 12.5 | 25 | 1.6 |

TABLE 1-continued

| Fungi Compound No. | MIC Values (γ/ml) | | |
|---|---|---|---|
| | Aspergillus fumigates | Candida albicans M-9 | Trichophyton asteroides |
| 41 | 6.2 | 3.1 | <0.1 |
| 42 | 3.1 | 12.5 | 3.1 |
| 43 | 1.6 | 12.5 | 3.1 |
| 44 | 3.1 | 12.5 | 3.1 |
| 45 | 6.2 | 25 | 3.1 |
| 46 | 6.2 | 25 | 3.1 |
| 47 | 6.2 | 12.5 | 1.6 |
| 62 | 0.8 | 25.0 | <0.1 |
| 66 | 6.2 | 12.5 | 0.2 |
| 67 | 6.2 | 6.2 | 0.2 |
| 68 | 6.2 | 12.5 | 3.1 |
| 69 | 12.5 | 25 | 1.6 |

Compounds (I) and their acid addition salts exhibit excellent antifungal activities against various phytopathogenic fungi and soil borne pathogens and are useful as agricultural fungicides.

1. Control Test to Botrytis rot(gray mold) of Cucumber (1) Test Method

A seed of cucumber (cultivar:Matsukaze) was sown in a vinyl chloride-cup of 9 cm in diameter containing soil in a greenhouse and cultivated. At the primary leaf stage, 2.5 ml each of the solution containing a prescribed concentration of the test compound was applied over the above cucumber, which was kept at 25° to 26° C. in 80% humidity for 24 hours. A suspension of *Botrytis cinerea* spores was inoculated onto the leaves at five spots per leaf and the leaves were kept at 80° C. in 95% humidity for 72 hours.

(2) Results

The results are shown by percent disease control (%) calculated from the diseased degree according to the following formula.

Percent Disease Control (%) = $\dfrac{\text{(Diseased Degree in Untreated Plot)} - \text{(Diseased Degree in Treated Plot)}}{\text{Diseased Degree in Untreated Plot}} \times 100$ The compounds numbered in the following Table 2 each have the same structure as that of the compounds in the corresponding numbered Examples.

TABLE 2

| Compd. No. | Concentration (ppm) | Diseased Degree | Percent Disease Control (%) |
|---|---|---|---|
| 1 | 500 | 0 | 100 |
| 3 | " | " | " |
| 6 | " | " | " |
| 7 | " | 40 | 60 |
| 8 | " | 0 | 100 |
| 15 | " | " | " |
| 17 | " | " | " |
| 24 | " | " | " |
| 27 | " | " | " |
| 34 | " | " | " |
| 61 | " | " | " |
| 62 | " | " | " |
| untreated | — | 100 | 0 |

(Note)
Diseased degrees were calculated according to the subsequent formula:

| Disease condition | Marks | Numbers examined |

TABLE 2-continued

| | | |
|---|---|---|
| Largely faded lesions formed at inoculated parts | 20 | a |
| Back of the inoculated leaf faded | 10 | b |
| Back of the inoculated leaf slightly faded | 5 | c |
| No disease | 0 | d |

$$\text{Diseased Degree} = \frac{20a + 10b + 5c + 0d}{(a+b+c+d) \times 20} \times 100$$

2. Control Test to Anthracnose of Cucumber (1) Test Method

A seed of cucumber (cultivar:Matsukaze) was sown on a vinyl chloride-cup of 9 cm in diameter in a greenhouse containing soil and cultivated. At the primary leaf stage, 2.5 ml each of the solution containing a prescribed concentration of the test compound was applied over the above cucumber, which was kept at 25° to 26° C. in 80% humidity for 24 hours. A suspension of *Colletotrichum lagenarium* spores was inoculated onto the above leaves at five spots per leaf and the leaves were kept at 25° C. in 95% humidity for 1 day and at 25° C. in 75 to 80% humidity for 6 days.

(2) Results

Percent disease control (%) was calculated as mentioned in the above test 1.

TABLE 3

| Compd. No. | Concentration (ppm) | Diseased Degree | Percent Disease Control (%) |
|---|---|---|---|
| 46 | 500 | 20 | 80 |
| 58 | " | 0 | 100 |
| untreated | — | 100 | 0 |

3. Control Test to Powdery Mildew of Cucumber (1) Test Method

A seed of cucumber (cultivar:Matsukaze) was sown in a vinyl chloride-cup of 9 cm in diameter containing soil in a greenhouse and cultivated. At the primary leaf stage, 5 ml each of a solution of the test compound in a prescribed concentration was applied over the above cucumber, which was kept at 25° to 26° C. for 1 day. Primary leaves of cucumber previously infected by pathogenic fungi of the powdery mildew (*Shpaerotheca fuliginea*) were taken and those having lesions covered with spores were cut out in 1 square centimeter pieces, which were stuck to the primary leaves in the cups for inoculation, four plots per leaf. The above treated leaves were kept at 25° to 26° C. for 10 days.

The spore formation on the inoculated plots was observed by a microscope.

Standard of the evaluation:
(+): Formation of many spores and hypae observed on the inoculated plots
(−): Neither infected spots nor spore formation observed on the inoculated plots (2) Results

| Compd. No. | Concentration (ppm) | Diseased Degree |
|---|---|---|
| 5 | 500 | − |
| 21 | " | − |
| 36 | " | − |
| 78 | " | − |
| 80 | " | − |
| untreated | — | + |

4. Control Test against rice plant blast (1) Test Method

Seedlings of rice plants (cultivar:Aichi-asahi) reared in a greenhouse for 10 days were transplanted in a vinyl chloride-cup of 9 cm in diameter. A solution of the test compound at a prescribed concentration was applied to the above rice plants 14 days after the transplanting. One day after the application, a spore suspension of pathogenic fungi of rice plant blast (*Pyricularia oryzae*) sprayed on the leaf blades of the seedlings, which were kept at 28° C. in 98% humidity for 24 hours and at 28° C. in 90% humidity for 7 days in a greenhouse. The number of infected spots on the inoculated leaves was observed.

(2) Results

The results are shown by percent disease control which was calculated according to the following formula:

$$\text{Percent Disease Control (\%)} = \frac{\left(\begin{array}{c}\text{Number of Spots}\\ \text{in Untreated Plot}\end{array}\right) - \left(\begin{array}{c}\text{Number of Spots}\\ \text{in Treated Plot}\end{array}\right)}{\text{Number of Spots in Untreated Plot}} \times 100$$

| Compd. No. | Concentration (ppm) | Number of Spots | Percent Disease Control (%) |
|---|---|---|---|
| 23 | 500 | 271 | 89.5 |
| 28 | " | 45 | 98.3 |
| 36 | " | 25 | 99.0 |
| 78 | " | 99 | 96.2 |
| untreated | — | 2589 | 0 |

V. How to Use

Compounds (I) or the salts thereof may be applied in a wide variety of oral or parenteral dosage forms solely or in admixture with additives such as diluents, carriers, dispersants and the like. The pharmaceutical compositions may be in the form of solutions, suspensions, powders, granules, tablets, injections, ointments, tinctures, and the like. The formulations may be dispensed in a conventional manner. For example, Compounds (I) may be administered at a dose of 100 to 2000 mg per day for enteral application.

Further, compounds (I) and the salts thereof exhibit an excellent control effect against the following phytopathogenic fungi and other soil borne pathogens.

Rice plant: blast, damping-off, leaf spot
Wheat and barley: stem rust, loose smut, powdery mildew
Pear: red spot, scab, Alternaria leaf spot
Grape: gray rust, ripe rot, downy mildew, leaf spot, white rot, gray mold, powdery mildew Apple: Alternaria leaf spot, canker, black spot, red spot, blossom blight
Peach: brown rot
Cucumber: downy mildew, anthracnose, sclerotinia rot, gray mold, powdery mildew
Green pepper: powdery mildew
Tobacco: brown spot, powdery mildew Compounds (I) or the salts thereof may be formed to wettable powders, granules, powders, emulsions, tablets, aerosols, fumigations, oils, and the like solely or into admixture with additives or carriers ordinarily employed in agricultural fungicides. Compounds (I) may be applied to plants at a dose of 0.5 to 100 g per are.

The following examples are provided to further illustrate this invention.

EXAMPLE 1

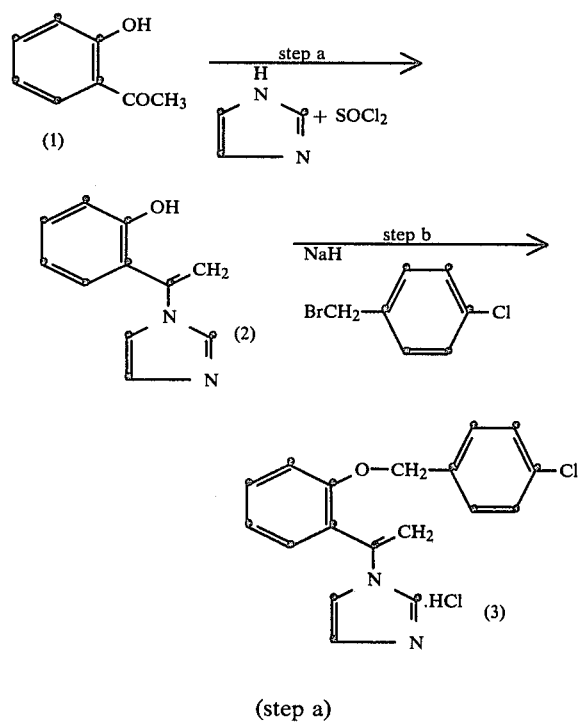

(step a)

To a solution of 60 g of imidazole in 300 ml of dry methylene chloride is added 26.2 g of thionyl chloride, and the mixture is stirred at room temperature for 10 minutes, mixed with 20 g of Compound (1), and stirred at room temperature for 1.5 hours. The reaction mixture is mixed with ice water and extracted with methylene chloride. The organic layer is washed with water, dried over Glauber's salt, and concentrated. The residue is dissolved in a mixture of 5% methanol and methylene chloride and chromatographed on a column of silica gel. The eluate is concentrated and the residue is washed with a mixture of ethyl acetate and isopropyl ether to give 25.8 g of Compound (2). mp. 150°–151° C.

IR: $\nu_{max}^{Nujol}$ 3300–2100, 2570, 1630 cm$^{-1}$.

(step b)

To a solution of the sodium salt of Compound (2) prepared from 500 mg of Compound (2), 164 mg of 60% sodium hydride and 5 ml of dry dimethylformamide is added 828 mg of p-chlorobenzyl bromide, and the mixture is stirred at room temperature for 15 minutes. The reaction mixture is mixed with ice water and extracted with methylene chloride. The organic layer is washed with water, dried over Glauber's salt, and concentrated. The residue is chromatographed on a column of silica gel, which is eluted with a mixture of 2% methanol and methylene chloride. The eluate is collected and mixed with a mixture of hydrochloric acid and ethanol, and the mixture is concentrated. The residue is crystallized from a mixture of ethyl acetate and ether and recrystallized from a mixture of methanol and ethyl acetate to give 345 mg of Compound (3) hydrochloride.

mp. 180.5°~181° C. (decomposition).

IR: $\nu_{max}^{Nujol}$ 2600 2300, 1649 cm$^{-1}$.

EXAMPLE 2

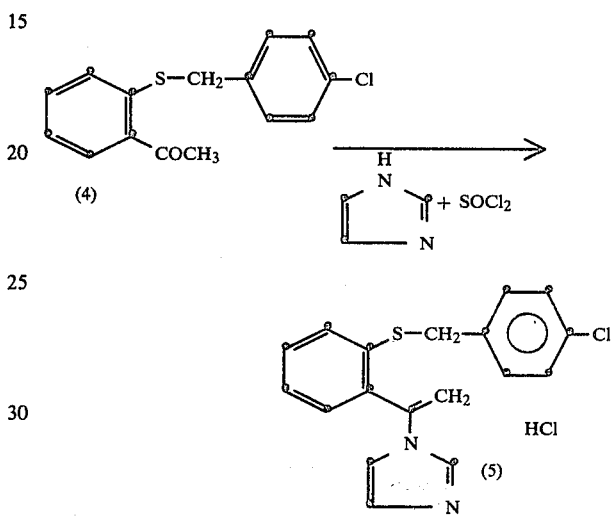

To a solution of N,N'-thionyldiimidazole prepared from 2.95 g of imidazole and 1.29 g of thionyl chloride in 15 ml of dry methylene chloride is added 2.0 g of Compound (4), and the mixture is extracted with methylene chloride. The organic layer is washed with water, dried over Glauber's salt, and concentrated. The residue is chromatographed on a column of silica gel, which is eluted with methylene chloride to recover 750 mg of unreacted Compound (4). The eluate from 1% methanol-methylene chloride to 2% methanol-methylene chloride is collected and concentrated, and the resulting residue is crystallized from ethanolic hydrochloric acid and recrystallized from methanol-ethyl acetate-ether to give 310 mg of Compound (5). mp. 153°–163° C.

EXAMPLE 3

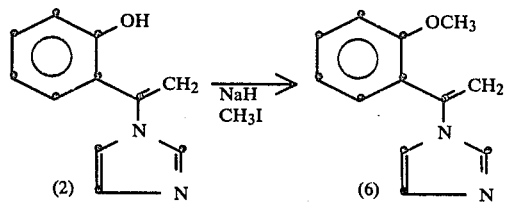

To a solution of 1 g of Compound (2) in 5 ml of dimethylformamide is added 322 mg of 60% suspension of sodium hydride in mineral oil with ice-cooling, and the mixture is stirred for 5 minutes, mixed with 1.14 g of methyliodide, and stirred at room temperature for 10 minutes. The reaction mixture is diluted with ice water and extracted with ether. The organic layer is washed with water, dried over Glauber's salt, and concentrated. The residue is chromatographed on a column of silica gel and eluted with 37% methanol-methylene chloride. The eluate is concentrated, and the residue is crystallized from hydrochloric acid-ethanol and recrystallized from methanol-acetic acid to give 520 mg of Compound (6).

mp. 190°–195° C.

Elemental Analysis (for $C_{12}H_{12}ON_2 \cdot HCl$): Calcd(%): C, 60.89; H, 5.54; N, 11.84; Cl, 14.98; Found(%): C, 60.78; H, 5.52; N, 11.73; Cl, 15.02.

EXAMPLES 4 TO 91

The following compounds are prepared in the same manner as mentioned in the above Examples.

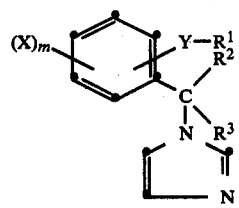

| Ex. No. | m | X | Y | R¹ | R² | R³ | Salt | mp (°C.) or IR |
|---|---|---|---|---|---|---|---|---|
| 4 | 0 | — | 2-O | —CH₂ | CH₃ | Im | — | 164–165 |
| 5 | " | " | " | —CH₂—C₆H₄—Cl | Ph | Im | " | 155–156 |
| 6 | " | " | " | —C₂H₅ | =CH₂ | | HCl·½H₂O | 159–162 |
| 7 | " | " | " | —n-C₃H₇ | " | | " | 146–148 |
| 8 | " | " | " | —n-C₄H₉ | " | | — | oily product $\nu^{film}$ 1638 cm⁻¹ |
| 9 | " | " | " | —(CH₂)₃—N(CH₃)₂ | " | | ½CH₃OH | oily product $\nu^{film}$ 1632 cm⁻¹ |
| 10 | " | " | " | —CH₂Ph | " | | HCl | 154–156 |
| 11 | " | " | " | —CH₂—C₆H₄—Cl | " | | — | 85–86 |
| 12 | " | " | " | " | " | | HCl | 180.5–181 |
| 13 | " | " | " | —CH₂—C₆H₄(Cl) | " | | " | 148.5–149 |
| 14 | " | " | " | —CH₂—C₆H₃(Cl)₂ | " | | " | 161–163 |
| 15 | " | " | " | —CH₂—C₆H₃(Cl)(Cl) | " | | " | 172–174 |
| 16 | " | " | " | —CH₂—C₆H₄—NO₂ | " | | — | 94–94.5 |
| 17 | " | " | " | —CH₂—C₆H₄—CH₃ | " | | HCl | 180–183 |
| 18 | " | " | " | —CH₂—C₆H₄—C₂H₅ | " | | " | 138–147 |
| 19 | " | " | " | —CH₂—C₆H₄—i-Pr | " | | — | oily product $\nu^{film}$ 1639 cm⁻¹ |
| 20 | " | " | " | —CH₂—C₆H₄—OCH₃ | " | | " | oily product $\nu^{film}$ 1630 cm⁻¹ |

-continued

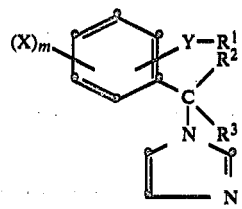

| Ex. No. | m | X | Y | R¹ | R² | R³ | Salt | mp (°C.) or IR |
|---|---|---|---|---|---|---|---|---|
| 21 | " | " | " | -CH₂-(thiophene) | " | | HCl | 139-142 |
| 22 | " | " | " | -CH₂-(5-chlorothiophene) | " | | " | 165-172 |
| 23 | " | " | " | -(CH₂)₂Ph | " | | (COOH)₂ | 122.5-124.5 |
| 24 | " | " | " | -(CH₂)₂-N(C₂H₅)₂ | " | | 2(COOH)₂ | 80-81 |
| 25 | " | " | " | -(CH₂)₂-N(CH₂Ph)₂ | " | | — | oily product ν$^{film}$ 1634 cm⁻¹ |
| 26 | " | " | " | -(CH₂)₂-N(morpholine) | " | | 2(COOH)₂ | 153.5-155 |
| 27 | " | " | " | -(CH₂)₂-OPh | " | | HCl | 158-160 |
| 28 | " | " | " | -(CH₂)₂-O-C₆H₄-Cl | " | | " | 140-142 |
| 29 | " | " | " | -(CH₂)₃-Ph | " | | — | oily product ν$^{film}$ 1639 cm⁻¹ |
| 30 | " | " | " | -(CH₂)₃-N(CH₃)₂ | " | | 2(COOH)₂ | 125-127 |
| 31 | " | " | " | -(CH₂)₃-N(C₂H₅)₂ | " | | " | 146.5-147.5 |
| 32 | " | " | " | -(CH₂)₃-O-C₆H₄-Cl | " | | — | oily product ν$^{film}$ 1635 cm⁻¹ |
| 33 | " | " | " | -(CH₂)₃-S-C₆H₄-Cl | " | | HCl | 138-140 |
| 34 | " | " | " | =CH₃ | ≡CH | CH₃* | — | oily product ν$^{film}$ 1660 cm⁻¹ |
| 35 | " | " | " | =CH₂Ph | ≡CH | CH₃*** | " | oily product ν$^{film}$ 1659 cm⁻¹ |
| 36 | " | " | " | =CH₂-C₆H₄-Cl | ≡CH | CH₃* | HCl | 175-177 |
| 37 | " | " | " | " | ≡CH | CH₃** | " | 185-187 |
| 38 | " | " | " | =CH₂-C₆H₄-Cl (2-Cl) | ≡CH | CH₃*** | — | oily product ν$^{film}$ 1658 cm⁻¹ |
| 39 | " | " | " | =CH₂-C₆H₃Cl₂ | ≡CH | CH₃*** | HCl | 156-158 |
| 40 | " | " | " | =CH₂Ph | ≡C(CH₃)₂ | | — | oily product ν$^{film}$ 1665 cm⁻¹ |

-continued

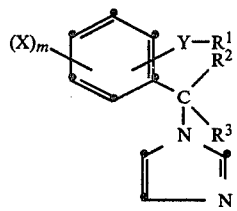

| Ex. No. | m | X | Y | R¹ | R² | R³ | Salt | mp (°C.) or IR |
|---|---|---|---|---|---|---|---|---|
| 41 | " | " | " | —CH₂—C₆H₄—Cl | " | | HCl | 137–138 |
| 42 | " | " | " | —CH₂—C₆H₄(Cl) (3-Cl) | " | | — | 62.5–64 |
| 43 | " | " | " | —CH₂—C₆H₃(Cl)₂ (2,4-di-Cl) | " | | " | 100–102 |
| 44 | " | " | " | —CH₂—C₆H₃(Cl)₂ (2,6-di-Cl) | " | | " | 100–101 |
| 45 | " | " | " | —CH₂—C₆H₄—CH₃ | " | | " | 58–60 |
| 46 | " | " | " | —(CH₂)₂—OPh | " | | " | 76–78 |
| 47 | " | " | " | —(CH₂)₃O—C₆H₄—Cl | " | | " | oily product $\nu^{film}$ 1670 cm⁻¹ |
| 48 | 1 | 4-Cl | " | —CH₃ | =CH₂ | | HCl.½H₂O | 193–196 |
| 49 | " | " | " | —CH₂—C₆H₄—Cl | " | | — | 132–133 |
| 50 | " | " | " | —(CH₂)₃—N(CH₃)₂ | " | | 2(COOH)₂ | 142–143.5 |
| 51 | " | 5-Cl | " | —CH₂—C₆H₄—Cl | H | Ph | — | 115–116 |
| 52 | " | " | " | —CH₂Ph | Ph | Im | — | 166.5–167 |
| 53 | " | " | " | —CH₂—C₆H₄—Cl | Ph | Im | — | 187–188 |
| 54 | " | " | " | —CH₂—C₆H₄—CH₃ | Ph | Im | — | 189–191 |
| 55 | " | " | " | —CH₂—C₆H₃(Cl)₂ | Ph | Im | — | 165–167 |
| 56 | " | " | " | —CH₂—C₆H₃(Cl)₂ | Ph | Im | — | 172–173.5 |
| 57 | " | " | " | —CH₂Ph | =CH₂ | | HCl.1/10H₂O | 174–175 |

-continued

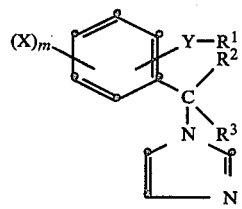

| Ex. No. | m | X | Y | R¹ | R² | R³ | Salt | mp (°C.) or IR |
|---|---|---|---|---|---|---|---|---|
| 58 | " | " | " | —CH₂—⌬—Cl | " | | " | 188–190 |
| 59 | " | " | " | —CH₂—⌬—CH₃ | " | | HCl.H₂O | 172–174 |
| 60 | " | " | " | —CH₂—[thiophene-Cl] | " | | HCl | 165–172 |
| 61 | " | " | " | —CH₃ | " | | " | 239 |
| 62 | " | " | " | —n-C₃H₇ | | | " | 178–181 |
| 63 | " | " | " | —CH₂Ph | =CH | CH₃*** | " | 132–134 |
| 64 | " | " | " | —CH₂—⌬—Cl | " | | " | 211–212 |
| 65 | " | " | " | —CH₂—⌬(Cl)(Cl) | " | | " | 170–174 |
| 66 | " | " | " | —CH₂Ph | =C(CH₃)₂ | | " | 192–193.5 |
| 67 | " | " | " | —CH₂—⌬—Cl | " | | " | 201–203 |
| 68 | " | " | " | —CH₂—⌬(Cl)(Cl) | " | | " | 193–194 |
| 69 | " | " | " | —CH₂—⌬—CH₃ | " | | — | 106–108 |
| 70 | " | " | " | —(CH₂)₃—O—⌬—Cl | " | | ½H₂O | oily product ν^film 1668 cm⁻¹ |
| 71 | " | " | " | —CH₃ | =CH | Ph | — | 118–118.5 |
| 72 | " | " | " | —CH₂Ph | =CH | C₂H₅*** | — | 158.5–159.5 |
| 73 | " | " | " | —CH₂—⌬—Cl | =CH | C₂H₅*** | HCl | 220–222 |
| 74 | " | " | " | —CH₂—⌬(Cl)(Cl) | =CH | C₂H₅*** | HCl | 166–167 |
| 75 | " | " | " | —(CH₂)₃—N(CH₃)₂ | =CH₂ | | 2(COOH)₂ | 105.5–107 |
| 76 | " | 4-OCH₂—⌬—Cl | " | —CH₂—⌬—Cl | " | | HCl | 193–195 |
| 77 | 2 | 3,5-Cl | " | —CH₂Ph | " | | " | 170–172 |

-continued

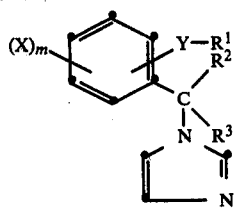

| Ex. No. | m | X | Y | R¹ | R² | R³ | Salt | mp (°C.) or IR |
|---|---|---|---|---|---|---|---|---|
| 78 | " | " | " | —CH₂—⟨phenyl⟩—Cl | " | " | " | 155–165 |
| 79 | " | " | " | —CH₂—⟨thienyl⟩ (S) | " | " | " | 170–171 |
| 80 | " | " | " | —CH₂—⟨Cl-thienyl⟩ (Cl, S) | " | " | " | 150–153.5 |
| 81 | " | " | " | —CH₂—⟨imidazolinyl (N,NH)⟩ | " | " | 2(COOH)₂·½H₂O | 153–154 |
| 82 | " | " | " | —(CH₂)₃—N(CH₃)₂ | " | " | 2(COOH)₂ | 119–120 |
| 83 | 0 | — | 3-O | —CH₂—⟨phenyl⟩—Cl | " | " | ½H₂O | oily product $\nu^{film}$: 1638 cm⁻¹ |
| 84 | " | " | 2-NH— | " | CH₃ | Im | — | 143.5–144 |
| 85 | " | " | " | " | =CH₂ | | " | 147–148 |
| 86 | " | " | 2-N(Tr)— | " | " | | " | 101–101.5 |
| 87 | 1 | 5-Cl | 2-O | —(CH₂)₃—N(CH₃)₂ | =C(CH₃)₂ | | 2(COOH)₂·CH₃CN | 101–104 |
| 88 | | 3,4 | " | —CH₂—⟨phenyl⟩—Cl | H | H | HCl | 166–167 |
| 89 | | 4,5 | " | " | H | H | — | 154–156 |
| 90 | | 5,6 | " | " | H | H | " | 142–143 |
| 91 | | 5,6 | " | " | =CH₂ | | — | 120–121 |

(Note)
The meanings of abbreviations are as follows:
Ph = phenyl  Im = imidazolyl  i-Pr = isopropyl  Tr = trifluoroacetyl
*means that methyl (ethyl, phenyl) group takes cis-form to imidazolyl group.
**means that methyl (ethyl, phenyl) group takes trans-form to imidazolyl group.
***means the mixture of cis- and trans-form.

REFERENCE EXAMPLE 1

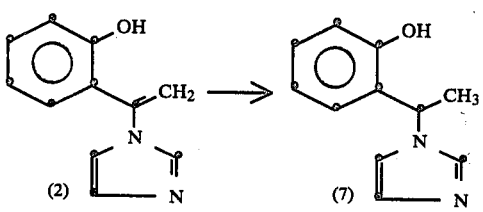

Compound (2) (500 mg) is hydrogenated in 14% hydrochloric acid-methanol (5 ml) in the presence of platinum oxide in a hydrogen stream. After the absorption of 1 mole of hydrogen, the reaction is stopped. The reaction is filtered and the filtrate is concentrated. The residue is mixed with aqueous sodium hydrogencarbonate solution and extracted with methylene chloride. The organic layer is washed with water, dried over Glauber's salt and concentrated. The residue is crystallized from ethyl acetate-isopropyl ether to give Compound (7) (456 mg).

mp. 170.5°~172° C.

REFERENCE EXAMPLE 2

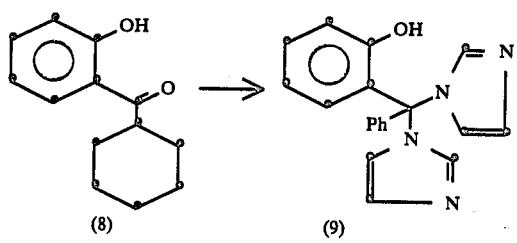

To a solution of N,N'-thionyldiimidazole prepared from imidazole (4.12 g), thionyl chloride (1.8 g), and dry methylene chloride (20 ml) is added Compound (1) (2 g), and the mixture is allowed to stand at room temperature overnight. The reaction mixture is mixed with ice-water and extracted with methylene chloride. The organic layer is washed with water, dried, and concentrated. The residue is washed with ethyl acetate-ether to give Compound (9) (2.72 g).

mp. 183°~193° C.

Hydrochloride of Compound (9) (2HCl.H$_2$O).

mp. 124°~127° C.

The preparations for fungicides are as follows:

Preparation 1

A mixture of Compound (3) hydrochloride prepared in Example 1 (5 weight parts), clay (85 weight parts), and talc (10 weight parts) is pulverized and formulated into a dust.

Preparation 2

A mixture of a compound prepared in Example 8 (50 weight parts), diatomaceous earth (45 weight parts), and calcium alkylbenzenesulfonate (2.5 weight parts) is pulverized, admixed, and formulated into a wettable powder.

Preparation 3

A mixture of the compound prepared in Example 27 (30 weight parts), xylene (60 weight parts), and polyoxyethylene alkyl aryl ether (10 weight parts) is admixed and formulated into an emulsion.

Preparation 4

A mixture of the compound prepared in Example 3 (5 weight parts), clay (85 weight parts), and talc (10 weight parts) is pulverized and formulated into a dust.

Preparation 5

A mixture of the compound prepared in Example 48 (50 weight parts), diatomaceous earth (45 weight parts), and calcium alkylbenzenesulfonate (2.5 weight parts) is pulverized, admixed, and formulated into a wettable powder.

Preparation 6

A mixture of the compound prepared in Example 7 (30 weight parts), xylene (60 weight parts), and polyoxyethylene alkyl aryl ether (10 weight parts) is admixed and formulated into an emulsion.

Preparation 7

The compound prepared in Example 62 (10 weight parts) is dissolved in water (90 weight parts) to give a solution.

The preparations for antimycotics are as follows:

Preparation 8

| Cream: | | |
|---|---|---|
| The compound prepared in Example 13 | 10 g |
| Bees wax | 100 g |
| Cetyl alcohol | 50 g |
| 2-Octyldodecanol | 50 g |
| Propylene glycol | 300 g |
| Mixture (1:1 w/w) of sorbitan monostearate and polyoxyethylene sorbitan monostearate | 50 g |
| Mixture (1.9:0.2 w/w) of butyl paraben and methyl paraben | 2 g |
| Mixture (0.06:1.25:9 w/w/w) of phosphoric acid, sodium hydroxide and monosodium phosphate dihydrate | 10 g |
| Distilled water | 428 g |
| | 1000 g |

Preparation 9

| Gel: | | |
|---|---|---|
| Nitrate of the compound prepared in Example 13 | 10 g |
| Carbopol 940 (carboxyvinyl polymer) | 15 g |
| Ethanol | 100 g |
| Propylene glycol | 650 g |
| Triisopropanolamine | 10 g |
| Distilled water | 215 g |
| | 1000 g |

What we claim is:

1. A compound of the formula:

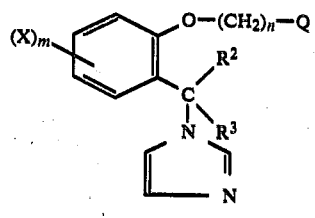

wherein

X is halogen;

m is an integer of 0 to 3;

n is an integer of 0 to 4;

Q is phenyl optionally substituted by 1 to 3 members selected from the group consisting of halogen, $C_1$–$C_5$ alkyl and $C_1$–$C_5$ alkoxy; and

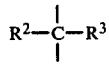

is 1-(1-imidazolyl)-1-phenylmethylene, or a pharmaceutically acceptable acid addition salt thereof.

2. The compound 1-[2-(4-chlorobenzyloxy)phenyl]-1,1-bis(1-imidazolyl)-1-phenylmethane.

3. The compound 1-(2-benzyloxy-5-chlorophenyl)-1,1-bis(1-imidazolyl)-1-phenylmethane.

4. The compound 1-[5-chloro-2-(4-chlorobenzyloxy)phenyl]-1,1-bis(1-imidazolyl)-1-phenylmethane.

5. The compound 1-[5-chloro-2-(4-methylbenzyloxy)phenyl]-1,1-bis(1-imidazolyl)-1-phenylmethane.

6. The compound 1-[5-chloro-2-(2,4-dichlorobenzyloxy)phenyl]-1,1-bis(1-imidazolyl)-1-phenylmethane.

7. The compound 1-[5-chloro-2-(3,4-dichlorobenzyloxy)phenyl]-1,1-bis(1-imidazolyl)-1-phenylmethane.

8. A fungicidal composition for agricultural application containing an effective fungicidal amount of the compound of claim 1 together with one or more inert carriers and/or adjuvants.

9. A method for controlling phytopathogenic fungi and other soil-borne pathogens which comprises applying the fungicidal composition of claim 8 to agricultural plants and/or fields.

* * * * *